(12) United States Patent
Fischer et al.

(10) Patent No.: US 6,228,613 B1
(45) Date of Patent: May 8, 2001

(54) STABLE FACTOR VIII/VON WILLEBRAND FACTOR COMPLEX

(75) Inventors: Bernhard Fischer, Vienna; Artur Mitterer, Mannsdorf; Friedrich Dorner; Johann Eibl, both of Vienna, all of (AT)

(73) Assignee: Baxter Aktiengesellschaft, Vienna (AT)

( * ) Notice: Subject to any disclaimer, the term of this patent is extended or adjusted under 35 U.S.C. 154(b) by 0 days.

(21) Appl. No.: 09/142,768

(22) PCT Filed: Mar. 13, 1997

(86) PCT No.: PCT/AT97/00055

§ 371 Date: Nov. 6, 1998

§ 102(e) Date: Nov. 6, 1998

(87) PCT Pub. No.: WO97/34930

PCT Pub. Date: Sep. 25, 1997

(30) Foreign Application Priority Data

Mar. 15, 1996 (AT) .................................................. 494/96

(51) Int. Cl.$^7$ ...................................................... C12P 21/06
(52) U.S. Cl. .................. 435/69.1; 435/69; 435/69.6; 435/68.1; 435/320.1; 435/252.3; 530/350; 530/383; 530/412; 530/413; 530/416; 530/381; 514/2; 514/12; 514/21; 514/834
(58) Field of Search .................................... 530/383, 413, 530/412, 350, 416, 381; 514/2, 834, 12, 21; 435/68.1, 69.6, 320.1, 69.1, 252.3, 69.9; 930/100; 260/112; 935/11, 60

(56) References Cited

U.S. PATENT DOCUMENTS

| | | | |
|---|---|---|---|
| 5,250,421 | * 10/1993 | Kaufman et al. | 435/69.6 |
| 5,854,403 | 12/1998 | Fischer et al. | 530/412 |
| 5,869,617 | 2/1999 | Fischer et al. | 530/381 |
| 5,872,099 | 2/1999 | Fischer et al. | 514/12 |
| 5,877,152 | 3/1999 | Fischer et al. | 514/12 |
| 5,880,265 | 3/1999 | Fischer et al. | 530/383 |
| 5,892,005 | * 4/1999 | Fischer et al. | 530/413 |
| 6,005,077 | 12/1999 | Schwarz et al. | 530/383 |

FOREIGN PATENT DOCUMENTS

| | | |
|---|---|---|
| 0600480A3 | 6/1994 | (EP) . |
| 0705846A1 | 4/1996 | (EP) . |
| WO86/01718 | 3/1986 | (WO) . |
| WO96/10584 | 4/1996 | (WO) . |

OTHER PUBLICATIONS

Josic et al., Journal of Chromatography B: Biomedical Applications, vol. 662, pp. 181–190, 1994.*

Wise et al., The Journal of Biological Chemistry, vol. 266, No. 32, pp. 21948–21955, 1991.*

Furlan et al., PNAS, vol. 90, pp. 7503–7507, Aug. 1993.*

Fischer et al. Thrombosis Research 84(1): 55–66 (1996).

* cited by examiner

Primary Examiner—Karen Cochrane Carlson
Assistant Examiner—Hope A. Robinson
(74) Attorney, Agent, or Firm—Heller Ehrman White & McAuliffe

(57) ABSTRACT

There are disclosed a stable factor VIII/vWF-complex, particularly comprising high-molecular vWF multimers, being free from low-molecular vWF molecules and from proteolytic vWF degradation products, as well as a method of producing this complex.

40 Claims, 9 Drawing Sheets

FIG. I vWF Multimer Analysis Before and After Anion Exchange Chromatography a: dissolved cryoprecipitate
b: Alu-supernatant
c: not bound to anion exchanger
d: 180 mM NaCl eluate +/− 10 mM $CaCl_2$
e: 200 mM NaCl eluate
f: 400 mM NaCl eluate Detection of Factor II in Individual Fractions
Before and After Anion Exchange Chromatography A: Factor II standard
B: dissolved cryoprecipitate
C: Alu-supernatant
D: 180 mM NaCl eluate
E: 400 mM NaCl eluate
F: 180 mM NaCl/+10 mM $CaCl_2$ eluate
G: 400 mM NaCl eluate Protein S in the Individual Fractions
Before and After Anion Exchange Chromatography A: Protein S standard
B: dissolved cryoprecipitate
C: Alu-supernatant
D: 180 mM NaCl eluate
E: 400 mM NaCl eluate
F: 180 mM NaCl/+10 mM $CaCl_2$ eluate
G: 400 mM NaCl eluate Factor IX in the Individual Fractions
Before and After Anion Exchange Chromatography A: Factor IX standard
B: dissolved cryoprecipitate
C: Alu-supernatant
D: 180 mM NaCl/10 mM CaCl$_2$ eluate
E: 400 mM NaCl eluate Plasminogen in Individual Fractions
Before and After Anion Exchange Chromatography A: Plasminogen standard
B: dissolved cryoprecipitate
C: 400 mM eluate anion exchanger
D: eluate lysine-Sepharose vWF-Multimer Analysis Before and After Heparin Affinity Chromatography A: Starting material before heparin affinity chromatography,
B: Factor VIII/vWF-complex eluate 160 mM NaCl,
C: Factor VIII/vWF-complex eluate 230 mM NaCl,
D: Factor VIII/vWF-complex eluate 300 mM NaCl

FIG. 7
vWF Multimer Analysis of p-vWF and r-vWF Before and After Heparin Affinity Chromatography
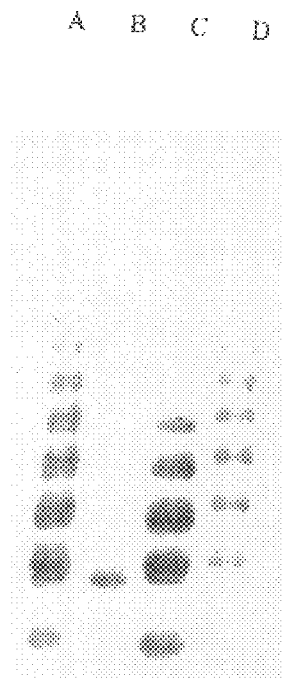
I. p-vWF
A: p-vWF starting material
B: p-vWF/LMW
C: p-vWF/MMW
D: p-vWF/HMW
II. r-vWF
A: r-vWF starting material
B: r-vWF/LMW
C: r-vWF/MMW
D: r-vWF/HMW Comparison of the Binding of r-vWF/HMW and p-vWF/HMW to Platelets Graphical representation of the amount of vWF added and of the platelet-bound amount of vWF Binding of p-vWF/HMW and r-vWF/HMW to Platelets and Multimer Analysis A: p-vWF/HMW;
B: r-vWF/HMW;
a: vWF, not bound;
b: platelet-bound vWF
c: vWF starting fraction after affinity chromatography

STABLE FACTOR VIII/VON WILLEBRAND FACTOR COMPLEX

The invention relates to a stable virus-safe factor VIII-complex, particularly comprising high-molecular vWF multimers of high structural integrity and free from low-molecular vWF molecules and from proteolytic vWF degradation products. Furthermore, the invention relates to a method of recovering and producing a stable factor VIII complex as well as pharmaceutical preparations thereof.

The coagulation of blood is a complex process including the sequential interaction of a number of components, in particular of fibrinogen, factor II, factor V, factor VII, factor VIII, factor IX, factor X, factor XI and factor XII. The loss of one of these components or the inhibition of its functionality leads to an increased tendency of hemorrhaging which may be life-threatening for some patients.

Von Willebrand factor (vWF) circulates in plasma complexed with factor VIII, factor VIII aiding the coagulation of blood and vWF in the complex with factor VIII stabilizing the latter and protecting it from proteolytic degradation. By its function in platelet aggregation, vWF also directly interferes in the coagulation of blood. vWF is a glycoprotein formed in different mammalian cells and subsequently released into circulation. Starting from a polypeptide chain having a molecular weight of approximately 220 kD, a vWF dimer having a molecular weight of 550 kD is formed in the cells by formation of several sulfur bonds. From the vWF dimers, further polymers of vWF of ever increasing molecular weights, up to 20 million Daltons, are formed by linkage. Therefore, vWF exists in plasma in a series of multimer forms having molecular weights of from $1 \times 10^6$ to $20 \times 10^6$ Daltons. It is assumed that particularly the high-molecular vWF multimers are of essential importance in the coagulation of blood.

Besides the carrier function for coagulation factor VIII, vWF has the functions of bridge formation between vessel wall and the platelets and of platelet agglutination. The basis for platelet agglutination is given by the binding of vWF to surface receptors (glycoproteins Ib, IIb/IIIa). The binding site within vWF for binding to GP Ib is located in disulfide loop Cys(509)-Cys(695). It is known that platelet agglutination starts with the binding of vWF to glycoprotein Ib. Following an activation signal, binding of vWF to the glycoprotein IIb/IIIa-complex and agglutination occur. Binding of vWF to the surface receptors thus is a prerequisite for platelet agglutination; the binding of several platelets by a vWF molecule leads to agglutination. vWF-platelet binding thus constitutes the molecular cause for platelet agglutination.

In hemophilia, blood coagulation is disturbed by a deficiency of certain plasmatic blood coagulation factors. In hemophilia A, the tendency to hemorrhage is based on a deficiency of factor VIII or on a deficiency of vWF, respectively, which is an essential component of factor VIII. Treatment of hemophila A primarily is effected by replacing the lacking coagulation factor by factor concentrates, e.g. by infusion of factor VIII, factor VIII-complex or vWF.

vWF Syndrome has several clinical pictures which go back to an underproduction or overproduction of vWF. Thus, e.g., an overproduction of vWF leads to an increased thrombosis tendency, whereas an undersupply is caused by the absence or reduction of high-molecular forms of vWF which manifests itself by an increased hemorrhage tendency and an extended hemorrhaging period due to an inhibited platelet aggregation. The deficiency of vWF may also cause a phenotypical hemophila A, since vWF is an essential component of functional factor VIII. In these instances, the half-life of factor VIII is reduced so much that its function in the blood coagulation cascade is impaired. Patients suffering from von Willebrand disease (vWD) thus frequently exhibit a factor VIII deficiency. In these patients, the reduced factor VIII activity is not the consequence of a defect of the X-chromosomal gene, but is an indirect consequence of the quantitative and qualitative change of vWF in plasma. The differentiation between hemophilia A and vWF normally can be effected by measuring vWF antigen or by determining the ristocetin cofactor activity. Both, the vWF antigen content and the ristocetin cofactor activity is lowered in most vWD patients, whereas it is normal in hemophilia A patients.

Conventional methods for the therapy of von Willebrand syndrome are with vWF recovered from plasma, and there exists a number of suggestions to treat vWD patients with purified vWF or with factor VIII/vWF-complex.

Purification of factor VIII or of factor VIII-complex from plasma or from cryoprecipitate is even more difficult because factor VIII is present in plasma in very small amounts only, is extremely unstable, and the association of factor VIII with vWF is reversible under specific conditions. Factor VIII is recovered from plasma by purification and concentration, yet, depending on the purification method, instability and loss of factor VIII activity may occur because vWF and factor VIII are separated during purification. Thus, the final product frequently is a mixture of stable factor VIII-complex and unstable factor VIII, as well as of contaminating proteins, such as, e.g., fibrinogen, fibronectin or vitamin K-dependent proteins which could not be removed by the purification. Because of the instability of the purified complex, stabilizers, such as albumin or amino acids etc., are admixed. However, the presence of contaminating proteins and/or stabilizers in the purified product did reduce the specific activity of the factor VIII-complex.

EP 0 468 181 describes a method of purifying factor VIII from human plasma by ion exchange chromatography, elution of factor VIII with high ionic strength at acidic pH and collecting the eluate in the presence of a stabilizer, such as heparin, albumin and PEG and lysine or histidine as antiproteases. However, upon the addition of albumin, the specific activity decreases from 300–1200 U/mg protein to 18–24 U/mg protein.

Madaras et al. (Haemostasis 7:321–331 (1978)) describe a method of purifying factor VIII on heparin-Sepharose and eluting with increasing NaCl concentrations. However, the factor VIII thus obtained had merely low activity.

U.S. Pat. No. 5,252,709 describes a method of separating factor VIII, vWF, fibronectin and fibrinogen from human plasma, wherein at first factor VIII, vWF and fibronectin are bound to a DEAE-type ion exchanger and subsequently are eluted separately from the ion exchanger by increasing salt concentrations.

Zimmerman et al. (U.S. Pat. No. 4,361,509) have described a method of purifying factor VIII, wherein factor VIII/vWF-complex is bound to a monoclonal anti-vWF antibody and factor VIII is dissociated from the complex by means of $CaCl_2$ ions. The factor VIII thus obtained subsequently is recovered in pure form via a further chromatographic step, it must, however, be stabilized by the addition of human albumin.

By expressing factor VIII in recombinant cells (Wood et al. (1984), Nature 312:330–337), factor VIII could be produced by genetic engineering methods, yet only by the addition of or co-expression with vWF, a commercially usable yield of recombinant factor VIII could be obtained. To produce a pharmaceutical preparation, however, vWF is separated from factor VIII during the purification process up to a negligible residual amount, and the purified recombinant factor VIII is stabilized with albumin (Griffith et al. (1991), Ann. Hematol. 63:166–171).

For a use in the therapy of patients suffering from hemophilia A—and also from von Willebrand syndrome, a purified factor VIII, complexed with vWF, is desirable (Berntorp (1994), Haemostasis 24:289–297). In particular, it has repeatedly been emphasized that in preparations lacking vWF or having merely a low content of vWF, an extended bleeding time and a low factor VIII:C half-life are observed in vivo. Normalisation of vWF in vivo is important for maintaining the concentration of factor VIII in plasma both by reducing the factor VIII elimination rate and by aiding the liberation of endogenous factor VIII (Lethagen et al. (1992), Ann. Hematol. 65:253–259).

DE 3 504 385 describes carrying out an ion exchange chromatography for purifying factor VIII/vWF-complex, factor VIII-complex being bound via sulfate groups and eluted with citrated buffer, calcium chloride and NaCl gradient. In this instance, the factor VIII-complex is eluted from the carrier with a concentration of 0.5 M NaCl.

EP 0 416 983 describes the recovery of factor VIII/vWF-complex from human plasma by precipitation with a combination of barium chloride and aluminum hydroxide and subsequent anion exchange chromatography on DEAE-Fractogel.

In EP 0 411 810, purification of factor VIII/vWF-complex from cryoprecipitate is effected by means of heparin affinity chromatography and subsequent elution of the complex with calcium chloride. A further development of this method is described in WO 93/22337. To remove contaminating proteins, such as fibrinogen and fibronectin, a glycine/NaCl precipitation is carried out after the elution with $CaCl_2$.

To purify factor VIII/vWF-complex it has also been suggested to precipitate contaminating proteins, such as fibrinogen, with high concentrations of amino acids, in particular glycine, to dissociate factor VIII/vWF-complex which remains in solution by the addition of a calcium and amino acid-containing buffer, and subsequently to recover factor VIII and vWF separately from each other by anion exchange chromatography (WO 82/04395).

U.S. Pat. No. 5,356,878 describes the preparation of factor VIII-complex, in which contaminating proteins (fibrinogen, vitamin K-dependent factors or fibronectin) are separated by precipitation with $Al(OH)_3$ and PEG, factor VIII-complex is chemically virus-inactivated in the presence of glycine and NaCl, and subsequently the non-factor VIII-complex-specific proteins are removed by gel filtration.

Hornsey et al. (Thromb. Haemost. 57:102–105 (1987)) have purified factor VIII/vWF by means of immune affinity chromatography and attained a specific activity of 45 U of factor VIII/mg protein and 60 U of ristocetin activity/mg protein. However, the final product is contaminated with 4% of fibrinogen and with 2% of fibronectin and with murine antibodies detached from the carrier.

Mejan et al. (Thromb. Haemost. 59:364–371 (1988)) suggested to purify factor VIII/vWF-complex directly from plasma by immune affinity chromatography. The purified complex was stabilized with human serum albumin and subsequently lyophilized. With the elution conditions described, however, a partial liberation of the antibodies from the column was observed, which led to a contamination of the eluate with monoclonal antibodies and required a second purification step for removal of the antibodies. With their method, Mejan et al. attained an approximately 1400-fold enrichment of the factor VIII/vWF-complex with a specific factor VIII:C-activity and ristocetin activity of 20 U/mg protein each, the product containing all the vWF multimers. After stabilization of the complex with 10 mg/ml albumin, a stability of 3–4 months at $-20°$ C. was observed. However, it has been repeatedly emphasized that a particular difficulty in the purification of the complex consists in maintaining the association of the proteins, because both components in the complex are unstable.

Harrison et al. (Thromb. Res. 50:295–304 (1988)) describe the purification of factor VIII/vWF-complex by means of chromatography on dextran sulfate-agarose.

EP 0 600 480 describes the purification of factor VIII/vWF-complex by means of anion exchange chromatography, wherein the factor VIII/vWF-complex-containing eluate is stabilized with heparin and albumin and optionally lysine and histidine are added as antiproteases.

Commercially available factor VIII/vWF-preparations partially have no or only a small portion of high-molecular vWF multimers (vWF/HMW), and exhibit, particularly in dependence on the infusion time, in vivo a reduction of the high-molecular vWF multimers (Lethagen et al. (1992), Ann. Hematol. 65:253–259).

The factor VIII preparations described in the prior art do mostly contain the entire vWF multimer pattern, yet their portions of HMW-vWF and LMW-VWF vary and they exhibit so-called triplet structures, indicating a proteolytic degradation of vWF multimers, in particular of vWF/HMW (Scott et al. (1993), Sem. Thromb. Hemost. 19:37–47, Baillod et al. (1992), Thromb. Res. 66:745–755, Mannucci et al. (1992), Blood 79:3130–3137). The stability of these preparations is limited thereby.

To stabilize the preparations, either before virus inactivation or so as to obtain a storage-stable preparation, it has repeatedly been emphasized that the addition of a stabilizer, such as albumin, is required.

All the factor VIII concentrates that have been obtained by purification of the protein from human plasma or which have been in contact with biological material from mammals furthermore bear the potential risk of containing microbiological or molecular pathogens, such as, e.g., viruses. To produce a safe preparation therefore an inactivation of pathogenic organisms is also always necessary. Effective inactivation methods may easily also lead to a loss of the biologic activity of the factor VIII complex. Thus, Palmer et al. found (Thromb. Haemost. 63:392–402 (1990)) that in case of heat treatment for an effective virus inactivation, an activity loss of between 17% and 30% must be reckoned with also in the presence of a stabilizer.

It has repeatedly been emphasized that factor VIII/vWF-concentrates exhibiting an intact multimer structure possibly have a favorable influence on the hemorrhaging time, because they carry out the primary function of vWF, i.e. platelet agglutination, and have a higher affinity to the platelet receptors glycoprotein Ib and IIb/IIIa than low-molecular vWF multimers (LMW-vWF) (Mannucci et al. (1987), Americ. J. Hematology 25:55–65). However, there exists the problem that there occurs a degradation particularly of the HMW-vWF molecules during the process of preparing factor VIII concentrates.

Thus, there is a need for a factor VIII-complex having a sufficient specific activity of factor VIII:C and vWF-activity, which has an improved stability and which remains stable over an extended period of time also without the addition of the non-factor VIII/vWF-complex-specific stabilizer.

It is thus the object of the present invention to provide a factor VIII/vWF-complex having an improved stability.

According to the invention, this object is achieved by providing a factor VIII/vWF-complex which particularly contains high-molecular vWF multimers and which is free from low-molecular vWF molecules and from proteolytic vWF degradation products.

The specific platelet agglutination reflects the ratio of ristocetin cofactor activity and vWF antigen content. A high specific platelet agglutination activity thus indicates the specific activity of the multimers. Within the scope of the present invention it could be shown both for plasmatic vWF (p-vWF) and for recombinant vWF (r-vWF) or factor VIII/vWF-complex, respectively that in case of a high multimerisation degree of vWF, the specific platelet agglutination (RistoCoF/vWF:ag) is substantially increased in comparison to low-molecular multimers.

Low-molecular p-vWF (p-vWF/LMW) and low-molecular r-vWF (r-vWF/LMW) exhibit only very low platelet agglutination.

This situation can be explained more clearly by the fact that on account of the short vWF chain, no stable connection between several platelets will occur. On the contrary, high-molecular (long) vWF multimers are able to connect several platelets in a stable manner.

It has been shown that both, high-molecular p-vWF (p-vWF/HMW) and high-molecular r-vWF (r-vWF/HMW) bind to platelets in a concentration-dependent manner and exhibit a higher specific platelet agglutination activity than low-molecular vWF multimers.

The stable factor VIII/vWF-complex according to the invention therefore has a specific vWF platelet agglutinating activity of at least 50 U/mg vWF:Ag.

In plasma, factor VIII/vWF in complex occurs at a molar ratio of approximately 1:50. It has been found that this ratio is necessary in plasma to offer a good protection against proteolytic degradation, in particular by protein C (Vlot et al. (1995), Blood 85:3150–3157).

According to a further aspect of the present invention, the factor VIII/vWF-complex of the invention has a molar ratio of factor VIII to vWF of between 0.01 and 100. This means that the complex exhibits a ratio of factor VIII molecules to vWF molecules of between 1:100 and 100:1, respectively. Preferably, the molar ratio of factor VIII to vWF ranges between 1:30 and 1:70, particularly preferably it is 1:50, and due to the high portion of vWF/HMW in the complex, an optimum ratio is obtained for a protection against proteolytic degradation.

According to the invention, furthermore a stable factor VIII/vWF-complex is provided which contains high-molecular plasmatic vWF multimers with doublet structure.

Within the scope of the present invention it has been found that from plasma or cryoprecipitate a chromatographically purified factor VIII-complex is obtained which is comprised of vWF multimer molecules exhibiting doublet structure. This has been surprising because vWF or factor VIII/vWF-complex purified from plasma or cryoprecipitate had only been known with a triplet structure of the vWF multimers. These triplet structures are created by proteolytic degradation of vWF multimers and indicate an instability of the vWF multimers. Palmer et al. (Thromb. Haemost. 63:392–402 (1990)) have described that in the preparation of factor VIII concentrate from heparinized plasma and subsequent virus inactivation, the normal triplet pattern changes, and the intensity of the triplet band having the lowest molecular weight increases greatly, indicating an increased proteolytic degradation of the vWF multimers. In contrast thereto, in the present invention a factor VIII/vWF is provided which completely lacks this vWF degradation product and which substantially contains the 2 bands of the original triplet having the higher molecular weight.

According to a further embodiment of the invention, a stable factor VIII/vWF-complex is provided which contains high-molecular recombinant vWF multimers exhibiting singlet structure. It has been found by multimer analysis that the vWF multimers of recombinant vWF merely have singlet structure, have a high structural integrity and are free from any proteolytic vWF degradation products. The factor VIII-complex according to the invention, containing high-molecular recombinant vWF molecules of high structural integrity therefore is very stable and is free from low-molecular vWF multimers and vWF degradation products.

The stable factor VIII/vWF-complex according to the invention is preferably free from plasma proteins, in particular from plasma proteases, and it is free from fibrinogen and fibronectin. Since plasma proteases and plasma proteins, in particular activated plasma proteins, such as protein C, factor IIa or factor IXa, vWF or factor VIII degrade proteolytically and the inventive complex is free from plasma proteins, it has an increased stability and integrity of the proteins in complex.

The complex according to the invention has an increased resistance to proteolytic degradation, and thus it is stable at room temperature, e.g., for at least 48 hours, preferably for at least 6 days, and in lyophilized form at 4° C. or room temperature for more than 2 years.

The factor VIII/vWF-complex according to the invention is so stable that it can be provided as a virus-safe complex. Virus safety is ensured by method steps for treating the complex for inactivation of viruses or for depletion of viruses, respectively.

For inactivating viruses, a heat treatment in solution or in the solid, preferably lyophilized, state is particularly suitable, and this heat treatment can reliably inactivate both lipid-enveloped and non-lipid-enveloped viruses. The complex according to the invention is, e.g., heat treated in the solid, wet state according to EP 0 159 311. Other methods for virus inactivation comprise also the treatment with detergents or with chaotropic substances, e.g. according to EP 0 519 901, WO 94/13329, DE 44 34 538 and EP 0 131 740.

According to a further aspect of the invention, a stable, virus-safe factor VIII-complex concentrate comprising in particular high-molecular vWF multimers of high structural integrity is provided. The high-molecular vWF multimers preferably have singlet or doublet structure and are free from low-molecular vWF multimers and from proteolytic degradation products of vWF. Surprisingly it has been shown that the factor VIII-complex concentrate according to the invention is so stable that a treatment for virus inactivation, e.g. as described above, negatively affects the stability of the proteins, in particular of the high-molecular vWF multimers in the complex only marginally and that thus the specific activity of factor VIII:C and vWF-ristocetin activity in the factor VIII-complex or factor VIII-complex concentrate is lowered only by 10% at the most in a virus inactivation step. In the hitherto known factor VIII-complex concentrates, a loss of activity of between 20 and 30% had to be reckoned with during the virus inactivation. In the neoantigen test, the factor VIII/vWF-complex of the invention did not exhibit any changes of the antigen structure after the virus inactivation step, which proves the stability of the proteins in the complex. On account of the high stability of the high-molecular vWF multimers, also a high specific platelet agglutination activity of at least 50 U/mg vWF:Ag is ensured in the factor VIII-complex concentrate according to the invention.

According to a special embodiment, the stable, virus-safe factor VIII-complex-concentrate of the invention contains factor VIII and vWF at a molar ratio of factor VIII to vWF of between 0.01 and 100, preferably between 0.05 and 1. In particular, the factor VIII-complex-concentrate is free from plasma proteins, in particular from plasma proteases, and free from microbiological and molecular biological pathogens.

To improve the stability of purified proteins, usually stabilizers, such as albumin, are added. When doing so, however, the specific activity of the purified protein is lowered by the addition of the foreign protein. vWF is a natural component of the factor VIII-complex. It has been found that by the addition of high-molecular vWF multimers (vWF/HMW) to a purified factor VIII fraction from plasma or from recombinant cell cultures, the stability of factor VIII is increased. Likewise it has been found that by the addition of vWF/HMW to a purified factor VIII-complex, the stability of the complex can be improved. Thus, one can do without the addition of commonly used stabilizers. In exceptions, optionally a protease inhibitor may be added also in the course of the recovery so as to maintain the intact structure, in particular of the vWF/HMW.

According to the invention, furthermore a pharmaceutical composition comprising a stable factor VIII/vWF-complex according to the invention or a virus-safe, stable factor VIII-complex-concentrate according to the invention can be provided.

In a special embodiment, the pharmaceutical composition contains a physiologically acceptable carrier or buffer. The formulation of the pharmaceutical preparation according to the invention may be effected in a common manner and as is known per se, e.g. by aid of salts and optionally amino acids, but also in the presence of tensides. On the basis of the above-described high stability of the complex, the stabilizers or protease-inhibitors commonly used may optionally also be done without in the pharmaceutical composition.

The stable factor VIII/vWF-complex according to the invention preferably is obtained as a highly purified product, which is obtained by chromatographic purification methods. In particular, chromatographic purification is effected by ion exchange chromatography and/or affinity chromatography. For this, i.a. materials for anion exchange, such as synthetic carrier materials or carbohydrate-based carriers, with ligands, such as DEAE, TMAE, QAE, Q or amino alkyl groups can be used, or carriers with immobilized substances which have a specific affinity to vWF can be used for affinity chromatography, respectively. Suitable affinity materials contain heparin, e.g.

According to a further aspect of the present invention, thus a method of recovering stable factor VIII/vWF-complex is provided. Therein, factor VIII/vWF-complex from a protein solution is bound at a low salt concentration to an affinity carrier, preferably a heparin affinity carrier, and stable factor VIII/vWF-complex is recovered at a high salt concentration. The complex preferably is bound to immobilized heparin at a salt concentration of $\leq 150$ mM, and is eluted at a salt concentration of a $\geq 200$ mM and $\leq 300$ mM. In a particularly preferred embodiment of the present invention, recovering of factor VIII/vWF-complex is carried out in a buffer system free from $CaCl_2$. In this manner factor VIII/vWF-complexes comprising low-molecular vWF molecules and high-molecular vWF molecules, respectively, can be selectively separated from each other, and factor VIII/vWF-complex comprising in particular high-molecular vWF molecules can be recovered at a higher salt concentration.

Soluble mono-and divalent salts are usable for elution. Preferably, NaCl is used. Calcium salts are not suitable for elution.

Preferably, the method according to the invention is carried out on a heparin affinity chromatography column. Any carrier to which heparin can be bound may be used for the affinity chromatography. AF-Heparin Toyopearl® (a synthetic, hydrophilic polymer of large pore size based on methacrylate) (Tosohaas), Heparin EMD Fraktogel® (a synthetic, hydrophilic polymer based on ethylene glycol, methacrylate and dimethyl acrylate) (Merck) or Heparin Sepharose Fast Flows® (containing natural dextran and agarose derivatives, respectively) (Pharmacia) have, e.g., proved useful.

In the method according to the invention, as buffer system, a buffer solution consisting of buffer substances, in particular Tris/HCl, phosphate buffer or citrated buffer, and optionally salt, is used, which is free from stabilizers, amino acids or other additives.

Affinity chromatography is preferably effected at a pH ranging from 6.0 to 8.5, preferably at pH 7.4.

In the method according to the invention, a protein solution comprising factor VIII/vWF-complex, such as, e.g., a plasma fraction, a cryoprecipitate or a cell-free culture supernatant derived from transformed cells is used. The solution may also be an enriched protein fraction of a chromatographic method.

According to the method of the invention for recovering factor VIII/vWF-complex, a factor VIII/vWF-complex may be obtained in an efficient and simple manner, which substantially comprises high-molecular vWF multimers. According to this method, thus a physiologically particularly active factor VIII/vWF-complex can be prepared in good yields and in high purity. The factor VIII/vWF-complex thus obtained is particularly characterized by a specific activity of factor VIII:C of at least 50 U/mg factor VIII:Ag and a specific vWF platelet agglutination activity of at least 50 U/mg vWF and is particularly free from low-molecular vWF multimers and from vWF degradation products.

According to a further aspect of the present invention, a method of recovering stable factor VIII/vWF-complex is provided, in which factor VIII/vWF-complex from an impure protein solution is bound to an anion exchanger and contaminating plasma proteins at a salt concentration of $\leq 200$ mM are selectively eluted in the presence of calcium salt. Subsequently, factor VIII/vWF-complex is obtained from the anion exchanger at a salt concentration of between a $\geq 200$ and $\leq 400$ mM. A factor VIII/vWF-complex substantially comprising high-molecular vWF multimers is recovered.

To carry out the method according to the invention, e.g. a plasma fraction, a cryoprecipitate or a culture supernatant from transformed cells which is free from cells can be used as the impure protein solution containing factor VIII/vWF-complex.

The contaminating proteins removed by the calcium salts are, in particular, plasma proteins, among them vitamin K-dependent factors, such as, e.g., factor II, factor IX, protein C, protein S, plasma proteases, such as plasminogen, fibronectin or fibrinogen. Removal of the unspecific proteins is particularly effected with $CaCl_2$ as calcium salt in the eluting agent at a concentration of between 1 mM and 15 mM, preferably of 10 mM.

It has been found within the scope of the present invention that the hitherto used method of aluminum hydroxide treatment for the separation of vitamin K-dependent proteins, fibrinogen or fibronectin is not sufficient to completely remove these proteins. By elution in the presence of calcium chloride, however, it has been ensured that these plasma proteins are substantially eliminated and a factor VIII/vWF-complex free from plasma proteins is recovered.

The anion exchange chromatography is preferably carried out at a pH range of from 6.0 to 8.5, preferably at a pH of 7.4.

Elution of the factor VIII/vWF-complex bound to the anion exchanger during the anion exchange chromatography preferably is carried out by increasing the salt concentration.

As the anion exchanger, preferably an anion exchanger of the quaternary amino type, in particular a Fractogel having tentacle structure, and in particular EMD-TMAE Fractogel, is used.

Preferably, factor VIII/vWF-complex is bound to the anion exchanger at a salt concentration of $\leq 200$ mM, and factor VIII/vWF-complex substantially comprising vWF/HMW is eluted at a salt concentration of $\geq 270$ mM, preferably at a $\geq 350$ mM. As the salts, soluble mono- and divalent salts are usable, NaCl being preferred.

Preferably, the factor VIII complex purified by anion exchange chromatography is further chromatographically purified by affinity chromatography, preferably on immobilized heparin, in a buffer solution comprised of buffer substances and, optionally, salt.

In a particular embodiment of the method according to the invention, at first a factor VIII/vWF-complex-containing fraction recovered from cryoprecipitate is bound to an anion exchanger, and factor VIII/vWF-complex substantially containing high-molecular vWF-multimers is eluted in enriched form after separation of the accompanying proteins, in particular of the plasma proteins. In a further purification step, the factor VIII/vWF-complex-containing eluate is contacted with an affinity carrier comprising covalently bound heparin, the complex binding to the carrier. After removal of foreign substances and foreign proteins by means of a suitable eluting agent, factor VIII complex is eluted from the affinity carrier by means of a mono- or divalent salt, preferably NaCl, in a buffer system.

In a further particular embodiment, the method is carried out with a factor VIII/vWF-complex obtained from recombinant cells. For this, a cell-free culture supernatant from cells which co-express factor VIII and vWF, or from co-cultured cells which have been transformed with factor VIII on the one hand and with vWF on the other hand can be used.

With the inventive method for recovering a highly purified stable factor VIII complex, a highly purified factor VIII/vWF-complex which is free from antibodies, free from plasma proteins, physiologically active and free from microbiological and molecular-biological pathogens can be obtained in a simple and efficient manner.

According to the present invention, the factor VIII/vWF-complex obtained from plasma or from recombinant cells particularly contains high-molecular vWF-multimers and is free from low-molecular vWF molecules and vWF degradation products. If the factor VIII/vWF-complex is recovered from plasma or from cryoprecipitate, the vWF/HMW are particularly comprised of doublet structures having high stability. Factor VIII/vWF-complex obtained from recombinant cells contains high-molecular vWF molecules having a singlet structure, high stability and structural integrity.

Thus, according to the present invention it is possible by means of defined chromatography steps to obtain FVIII/vWF free from other coagulation factors and from further plasma proteases. This has a favorable influence particularly on the purity and stability of the preparation. The factor VIII/vWF-complex obtained according to the invention thus is present in a particularly pure form. Preferably, the purity of the complex is at least 90%, particularly preferred 95%.

Due to the fact that the obtained factor VIII/vWF-complex is particularly stable on account of its high content of high-molecular vWF multimers and the absence of low-molecular multimers, vWF degradation products, foreign proteins, such as, e.g., plasma proteins, it is not necessarily required to add stabilizers to the purified product. Thus, the specific activity of the pure product is not lowered, e.g. when formulating the pharmaceutical composition, and it is avoided that possibly impurities or infectious particles are introduced into the product by the addition of foreign proteins.

In a further aspect of the invention, a method of preparing a stable factor VIII/vWF-complex is provided. In doing so, a purified high-molecular fraction of vWF molecules is added to a factor VIII or factor VIII complex purified via a chromatographic method, whereby a factor VIII/vWF-complex is obtained having a molar ratio of factor VIII to vWF/HMW of between 0.01 (corresponds to 1 factor VIII:100 vWF) and 100 (corresponds to 100 factor VIII:1 vWF), preferably of between 0.03 (1:30) and 0.07 (1:70), particularly preferred of 0.05 (1:50).

The factor VIII or factor VIII-complex purified via a chromatographic method may be derived from a plasma fraction, a cryoprecipitate or a cell-free cell culture supernatant from transformed cells.

The high-molecular fraction of vWF molecules used for the method of preparing the stable complex may be derived from plasma, a plasma fraction, a cryoprecipitate or a cell-free culture supernatant from transformed cells. The purified high-molecular fraction of vWF molecules contains preferably a specific platelet agglutination activity of at least 50 U/mg vWF:Ag, particularly preferred of at least 80 U/mg vWF:Ag.

To prepare the stable factor VIII complex, a purified fraction containing factor VIII or factor VIII/vWF-complex is mixed with a purified high-molecular fraction of vWF molecules at a desired molar ratio. For this, the content of vWF, factor VIII, the factor VIII activity and specific vWF activity are determined in the respective fractions, and the desired mixing ratio is adjusted by adding the respective amount of vWF/HMW. Preferably, mixing is effected such that a factor VIII/vWF-complex forms which has a molar ratio of factor VIII to vWF of between 1:100 and 100:1, preferably of 1:50.

According to the present invention, however, also a factor VIII/vWF-complex may be prepared which has a certain ratio of specific factor VIII:C activity to specific vWF-platelet agglutination activity. Particularly preferred is a complex having a ratio of specific acitivities of 1:1. Providing the desired mixing ratio is within the general knowledge of a skilled artisan.

The stable, virus-safe factor VIII-complex as well as the factor VIII-complex concentrate provided according to the present invention may be used both for the treatment of hemophilia A and for the treatment of von Willebrand syndrome. Since the factor VIII-complex-preparation according to the invention substantially contains high-molecular vWF molecules, it is particularly suitable for the treatment of vWD type II.

Due to the high portion of high-molecular vWF multimers, the complex of the invention also has very good pharmokinetics, since the vWF/HWM have a higher specific platelet agglutination and stability in vitro and in viva and stabilize factor VIII both in vitro and in vivo. The stability and structural integrity of the vWF multimers in the complex yields an improved half-life of the vWF and, in particular, also of factor VIII, whereby optionally the intervals of administering the pharmaceutical preparation of the invention can be reduced. Thus, particularly the occurrence of inhibitory antibodies to factor VIII in hemophilia A patients, e.g. on account of frequent administration of factor VIII concentrates, is prevented.

The invention will now be explained in more detail by way of the following examples as well as the drawing figures, while, however, not being restricted to the same.

FIG. 7 shows the multimer analysis of p-vWF and r-vWF before and after heparin affinity chromatography.

EXAMPLE 1

Purification of Factor VIII/vWF-complex by Anion Exchange Chromatography 10 g of cryoprecipitate were dissolved with 70 ml Na acetate, pH 7.0, 160 mM NaCl and 50 U/ml heparin at 30° C. for 10 min and incubated for further 30 minutes at room temperature until its complete dissolution. The solution was cooled to 15° C. and centrifuged until undissolved components had been removed, and the supernatant was treated with aluminum hydroxide gel. The solution was bound to a Fractogel EMD TMAE anion exchanger, and the anion exchanger was washed with 180 mM NaCl and 200 mM NaCl to remove foreign proteins. vWF and FVIII as a complex were subsequently eluted by means of 400 mM NaCl. The factor VIII:C and vWF:RistoCoF activities of the starting material and of the individual fractions were determined and have been summarized in Table 1.

TABLE 1

Factor VIII:C and vWF:RistoCoF Activities of the Aluminum Hydroxide Supernatant and of the Fractions of the Anion Exchange Chromatography

| Sample | Volume (ml) | vWF:RistoCoF (mU/ml) | FVIII:C (mU/ml) |
|---|---|---|---|
| Alu supernatant | 147 | 1060 | 2970 |
| 180 mM eluate | 254 | — | — |
| 200 mM eluate | 210 | — | — |
| 400 mM eluate | 132 | 1590 | 2890 |

Figure 1:
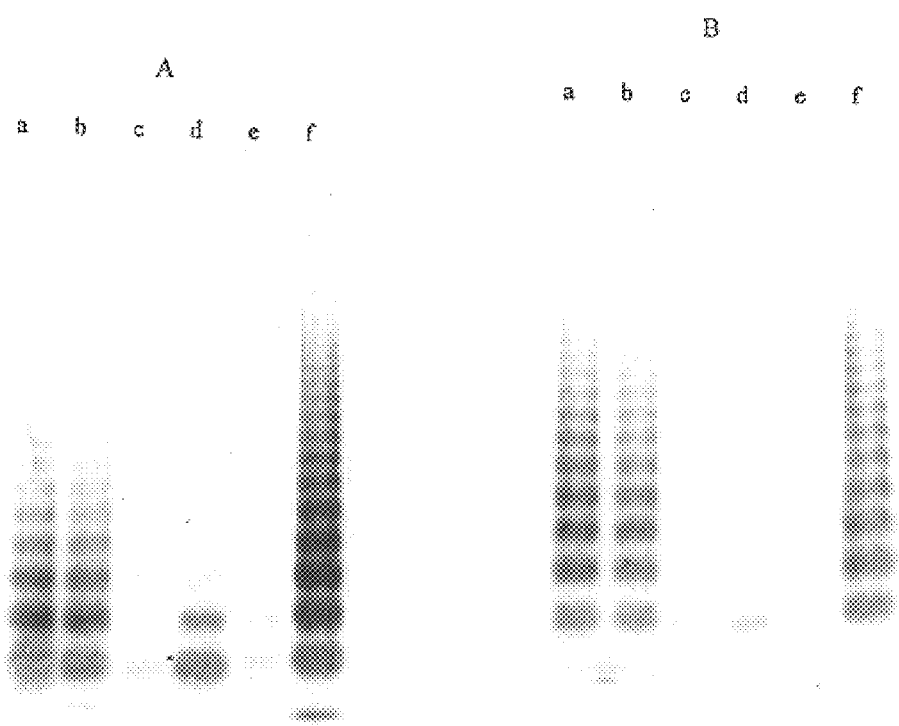
FIG. 1 shows an SDS-PAGE analysis of the vWF multimer pattern of the individual fractions before and after anion exchange chromatography.

By means of the anion exchange chromatography, factor VIII/vwF-complex could be obtained with an increased vWF:RistoCoF activity. To assay the vWF polymer pattern, the individual fractions of the anion exchange chromatography were analysed via SDS-PAGE (Laemmli (1970), Nature 227:680–685) (FIG. 1B). The polymer pattern of the vWF in the purified factor VIII/vWF-complex shows an identical band pattern and thus the same vWF polymer composition as in the cryoprecipitate. Thus, the purification did not lead to a proteolytic degradation of high-molecular vWF multimers in the complex.

EXAMPLE 2

Removal of Vitamin K-Dependent Proteins and Recovery of Highly Purified Factor VIII/vWF-complex The assays aimed at recovering a FVIII/vWF-complex free from proteases and other coagulation factors. As described in Example 1, dissolved cryoprecipitate was treated with aluminum hydroxide, and subsequently purified by means of anion exchange chromatography. To remove non-factor VIII/vWF-complex-specific proteins, 10 mM $CaCl_2$ were added during the elution with 180 mM NaCl. The factor VIII:C and vWF:RistoCoF activities of the starting material and of the individual fractions were determined and have been summarized in Table 2.

TABLE 2

Factor VIII:C and vWF:RistoCoF Activities of the Starting Material and of the Individual Fractions of the Anion Exchange Chromatography

| Sample | Volume (ml) | vWF:RistoCoF (mU/ml) | FVIII:C (mU/ml) |
|---|---|---|---|
| Alu supernatant | 146 | 1590 | 4250 |
| 180 mM eluate/ 10 mM $CaCl_2$ | 195 | — | — |
| 200 mM eluate | 127 | — | — |
| 400 mM eluate | 83 | 2120 | 5140 |

The eluates were assayed for their vWF multimer pattern by means of SDS-PAGE (FIG. 1A).

From the multimer analysis it is apparent that the 400 mM eluate contains the high-molecular vWF multimers, and starting from the cryoprecipitate, there does not occur any loss, in particular of high-molecular vWF multimers. By adding $CaCl_2$ ions, low-molecular vWF is separated, and a factor VIII complex containing a higher portion of high-molecular vWF molecules is obtained (FIG. 1A). Thus it is demonstrated that by the purification method, a proteolytic degradation of the high-molecular vWF multimers is avoided and by the addition of $CaCl_2$ ions it is possible to selectively remove low-molecular vWF molecules, such as, e.g., dimers or tetramers, whereby a factor VIII complex substantially comprising high-molecular vWF multimers is recovered.

The individual purification steps containing factor VIII/vWF-complex were analysed for the presence of vitamin K-dependent proteins before and during the anion exchange chromatography. To this end, individual. purification steps and the individual fractions were separated via SDS-PAGE, the proteins were transferred onto a membrane and the vitamin K-dependent proteins were detected by means of Western blot analysis.

a. Detection of Factor II in the Individual Purification Steps

To detect factor II in the individual fractions, polyclonal serum was used as the 1st antibody against factor II (Assera Faktor II, Stago), and detection was effected by means of alkaline phosphatase-conjugated polyclonal goat-anti-rabbit IgG HRP conjugate (Bio-Rad) as the 2nd antibody and subsequent chromogenic test.

Figure 2:
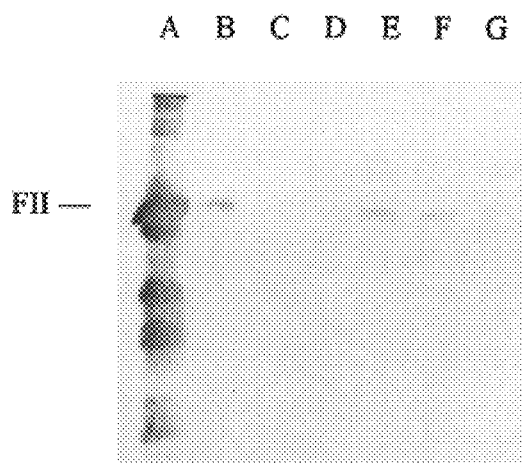
FIG. 2 shows the detection of factor II in individual fractions before and after anion exchange chromatography and after removal of factor II by calcium chloride elution.

From FIG. 2 it is apparent that cryoprecipitate contains factor II. Despite a preceding aluminum hydroxide precipitation, the latter is eluted from the anion exchanger (lane E) as an impurity at 400 mM NaCl (together with FVIII/vWF). It is, however, possible to selectively elute factor II by means of 10 mM $CaCl_2$ (lane F), and to recover vWF/FVIII at a subsequent elution with 400 mM NaCl free from factor II (lane G).

b. Detection of Protein S in the Individual Purification Steps

To detect protein S in the purification steps, polyclonal rabbit-anti-protein S serum (Assera Protein S, Stago) was used as the 1st antibody, and detection was effected with goat-anti-rabbit IgG HRP conjugate (Bio-Rad) as the 2nd antibody and subsequent chromogenic test.

Figure 3:
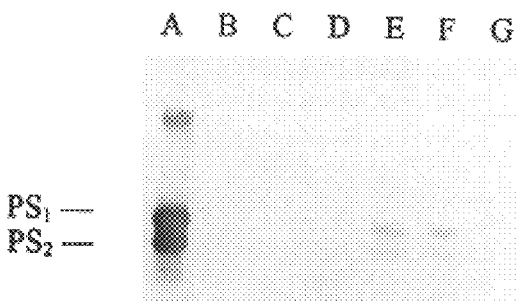
FIG. 3 shows the detection of protein S in individual fractions before and after anion exchange chromatography and after removal of protein S by calcium chloride elution.

FIG. 3 shows the detection of protein S in individual purification steps before and after the anion exchange chromatography and after removal of protein S by calcium chloride elution.

From FIG. 3 it is apparent that despite a preceding aluminum hydroxide precipitation, protein S from cryoprecipitate elutes at 400 mM NaCl (together with FVIII/vWF) from the anion exchanger (lane E) as an impurity. It is, however, possible to selectively elute protein S by means of 10 mM $CaCl_2$ (lane F), and to recover FVIII/vWF at a subsequent elution with 400 mM NaCl free from protein S (lane G).

c. Detection of Factor IX in the Individual Purification Steps

To detect factor IX in the purification steps, polyclonal rabbit-anti-factor IX serum (Assera Faktor IX, Stago) was used as the 1st antibody, and detection was effected by means of goat-anti-rabbit IgG HRP conjugate (Bio-Rad) as the 2nd antibody an subsequent chromogenic test.

Figure 4:
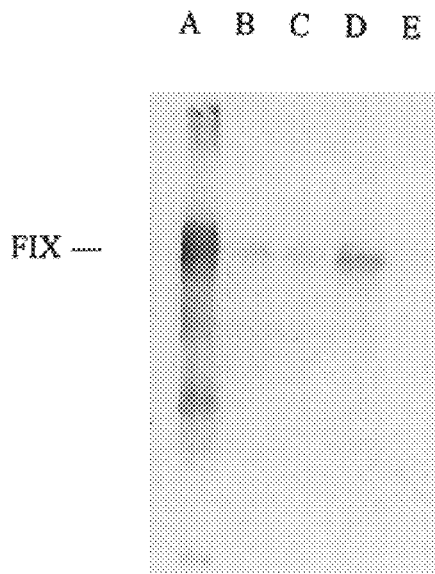
FIG. 4 shows the detection of factor IX in individual fractions before and after anion exchange chromatography and removal of factor IX by calcium chloride elution.

FIG. 4 shows the detection of factor IX in individual purification steps before and after anion exchange chromatography and selective removal of factor IX by calcium chloride.

From FIG. 4 it is apparent that factor IX elutes from the anion exchanger as contamination at 400 mM NaCl (together with factor VIII-complex) despite previous aluminum hydroxide precipitation. By adding 10 mM $CaCl_2$, factor IX, however, is selectively eluted (lane D), and FVIII/vWF is recovered free from factor IX (lane E) in the subsequent elution with 400 mM NaCl.

EXAMPLE 3

Removal of Plasma Proteases and Recovery of Highly Purified Factor VIII/vWF-complex The assays aimed at recovering a vWF/FVIII preparation free from proteases and from other coagulation factors. The protease plasminogen constitutes a substantial contamination of the cryoprecipitate. The former is also found in the FVIII/vWF eluate (400 mM eluate).

Figure 5:
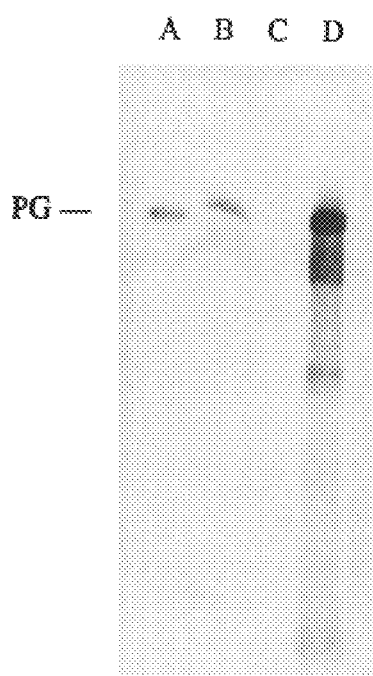
FIG. 5 shows the detection of plasminogen in individual fractions before and after anion exchange chromatography and removal of plasminogen by previous lysine-Sepharose chromatography.

To remove plasminogen, cryoprecipitate, as described above, was dissolved and treated with aluminum hydroxide gel. Subsequently, the Alu supernatant was filtered through a lysine-Sepharose gel, and from there it was directly applied onto the anion exchanger (Fractogel EMD TMAE). FVIII/vWF was eluted from the anion exchanger with 400 mM NaCl, as described before. The eluates from before and after the anion exchange chromatography were analysed for plasminogen by means of Western blot (FIG. 5). To this end, the proteins were separated by means of gel electrophoresis using SDS-PAGE, blotted onto a membrane, and plasminogen was detected with a polyclonal rabbit-anti-plasminogen serum (Stago) as the 1st antibody and subsequent chromogenic test.

From the results it is apparent that by filtration on lysine-Sepharose, the protease plasminogen is selectively separated from vWF/FVIII.

EXAMPLE 4

(Presently Considered by Applicant to be the Best Mode of Carrying out the Invention)

Heparin Affinity Chromatography of FVIII/vWF-complex

Fractogel AF EMD-heparin was used for the heparin affinity chromatography. FVIII/vWF which had been purified by anion exchange chromatography according to Example 2 (400 mM eluate) served as the starting material. To purify FVIII/vWF via affinity chromatography, 27 ml of the 400 mM NaCl Fractogel eluate were diluted 4-fold with 81 ml of Tris-HCl buffer (pH 7.4) and applied to the heparin affinity column. The column was first washed with 100 mM NaCl and subsequently, for removing unspecifically bound proteins, with 160 mM NaCl. Subsequently, the factor VIII/vWF-complex was obtained by elution of the heparin column with 300 mM NaCl. The factor VIII:C and vWF:RistoCoF activities as well as the vWF:Ag content in the starting material and in the individual fractions of the anion exchange chromatography and the heparin affinity chromatography were determined and have been summarized in Tables 4A and 4B.

TABLE 4A

Factor VIII:C and vWF:RistoCoF Activities of the Starting Material and of the Individual Fractions before and after Anion Exchange Chromatography

| Sample | Volume (ml) | vWF:Ag (µg/ml) | vWF:RistoCoF (mU/ml) | FVIII:C (mU/ml) |
|---|---|---|---|---|
| Alu supernatant | 75 | 55 | 1700 | 5260 |
| 180 mM eluate/ 10 mM $CaCl_2$ | 64 | 21 | 43 | — |
| 200 mM eluate | 33 | 1 | — | — |
| 400 mM eluate | 29 | 137 | 4250 | 9500 |

TABLE 4B

Factor VIII:C and vWF:RistoCoF
Activities of the Starting material and of the
Individual Fractions before and after Heparin Affinity
Chromatography

| Sample | Volume (ml) | vWF:Ag (μg/ml) | vWF:RistoCoF (mU/ml) | FVIII:C (mU/ml) |
|---|---|---|---|---|
| Starting material | 104 | 42 | 850 | 2630 |
| 160 mM eluate | 42 | 11 | 43 | 650 |
| 300 mM eluate | 28 | 92 | 2550 | 5840 |

Figure 6:
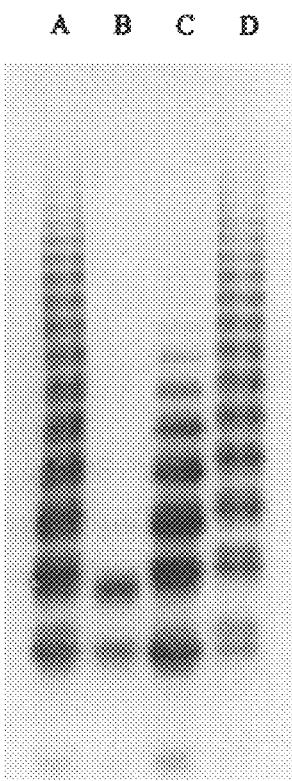
FIG. 6 shows SDS-PAGE analysis of the vWF multimer pattern of the individual fractions before and after heparin affinity chromatography.

The eluates of the heparin affinity chromatography were assayed for vWF polymer composition (FIG. 6).

From FIG. 6 it is apparent that the high-molecular portion of vWF is obtained in the 300 mM NaCl fraction. This fraction also has the highest factor VIII:C and vWF ristocetin cofactor activities (Table 4B).

From the sum of the results it is clearly apparent that by the combination of anion exchange chromatography and heparin affinity chromatography vWF, FVIII and also their complex can be isolated from the cryoprecipitate and purified. Particularly by means of heparin affinity chromatography it is possible to separate low-molecular vWF multimers and degradation products of vWF from cryoprecipitate.

EXAMPLE 5

Determination of the Specific Ristocetin Cofactor Activity of Purified vWF or vWF Complex Plasmatic vWF (p-vWF) from human cryoprecipitate and recombinant vWF (r-vWF) from the fermentation supernatant of recombinant CHO cells were isolated by means of chromatographic methods and purified according to Example 2. By heparin affinity chromatography and elution with various salt concentrations, fractions of various polymerisation degrees of vWF were isolated (according to Example 4). On the whole for p-vWF and r-vWF, fractions with low molecular weight vWF (vWF/LMW) were obtained at 120 mM NaCl, with medium molecular weight (vWF/MMW) at 230 mM NaCl and with high molecular weight (vWF/HMW) at 300 mM NaCl. These fractions were assayed for their content of vWF:Ag by means of ELISA (Asserachrom vWF®, Boehringer Mannheim), for ristocetin cofactor activity (vWF reagent, Behringwerke), their multimer structure by means of SDS-PAGE and for their platelet binding.

FIG. 7 shows the vWF polymer analysis of plasmatic vWF and of recombinant vWF.

It is particularly striking that before the purification of plasmatic vWF in cryoprecipitate the vWF dimers, tetramers or multimers are present in triplet structures. These triplet structures are degradation products of vWF multimers and are due to proteases present in plasma. Particularly with the vWF MMW and vWF HMW fractions, after purification only multimers with doublet structures are recognizable. Thus, by the chromatographic methods, vWF multimers having an altered composition and structure as compared to vWF molecules occurring in plasma are obtained, which is due to a depletion of proteases and low-molecular vWF degradation products.

As compared to plasmatic vWF multimers, recombinant vWF clearly shows the presence of only one singlet band in the vWF multimers. The recombinant vWF multimer molecules exhibit a high structural integrity and do not contain any proteolytic degradation products, as compared to the vWF triplet structures of plasmatic vWF known from the literature.

Table 5 and Table 6 show the specific ristocetin cofactor activity (RistoCoF/vWF:Ag) for p-vWF and r-vWF.

TABLE 5

Specific Ristocetin Cofactor Activity for Various p-vWF Fractions

| Sample | Specific RistoCoF Activity (mU RistoCoF/vWF:Ag) |
|---|---|
| p-vWF/LMW | 3 |
| p-vWF/MMW | 10 |
| p-vWF/HMW | 56 |

TABLE 6

Specific Ristocetin Cofactor Activity for Various r-vWF Fractions

| Sample | Specific RistoCoF Activity (mU RistoCoF/vWF:Ag) |
|---|---|
| r-vWF/LMW | 1 |
| r-vWF/MMW | 6 |
| r-vWF/HMW | 41 |

EXAMPLE 6

Binding of p-vWF and r-vWF to Platelets

Figure 8:
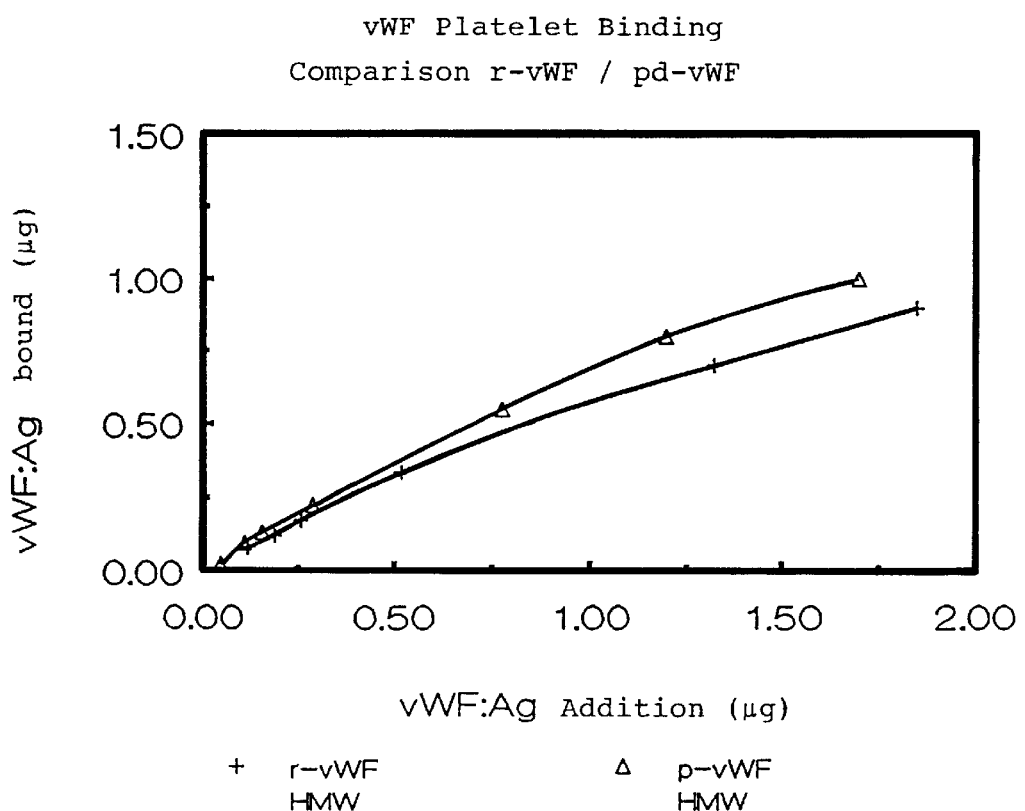
FIG. 8 shows the comparison of the binding of r-vWF/HMW and p-vWF/HMW to platelets and the graphic representation of the added amount of vWF and platelet-bound amount of vWF.
Figure 9:
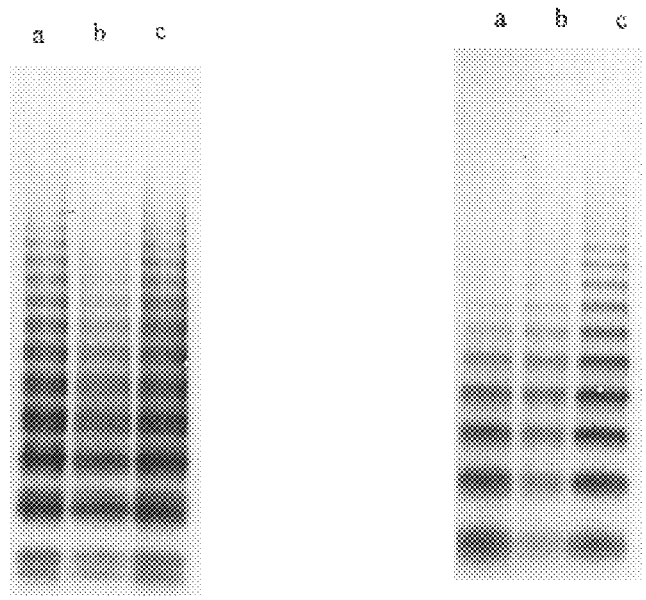
FIG. 9 shows the binding of p-vWF/HMW and r-VWF/HMW to platelets and multimer analysis.

In a further test, the binding of p-vWF and r-vWF to platelets was investigated. p-vWF/HMW and r-vWF/HMW, respectively, were incubated at constant concentrations of platelets and ristocetin. Subsequently, the platelets were separated by centrifugation (platelet sediment, bound vWF), and a supernatant (non-bound vWF) was obtained. In the starting material and in the supernatant vWF:Ag and the platelet-bound amount of vWF were determined. As a control, identical incubations were carried out without ristocetin. These did not yield any vWF platelet bonds. The ratio of the vWF concentration in the incubation formulation and of platelet-bound vWF is illustrated in FIG. 8 and shows the binding behaviour of p-vWF/HMW and r-vWF/HMW in a direct comparison. Following the incubation, both the supernatants (non-bound vWF) and the vWF in the platelet sediment (bound vWF) were assayed for their multimer composition. The results of the multimer analysis have been assembled in FIG. 9.

EXAMPLE 7

Determining the Stability of Purified Factor VIII/vWF-complex

Fractions obtained by means of anion exchange or heparin affinity chromatography were tested for the stability of the vWF multimers as well as for their factor VIII activity. For this purpose, the fractions obtained in the individual purification steps were stored at −20° C., 4° C. and room temperature for a period of time of up to 60 days, and after 0, 1, 3, 5, 10, 15, 20, 30 and 60 days samples were each subjected to a vWF multimer analysis, a factor VIII:C and a vWF ristocetin cofactor activity determination. There, the eluates of the anion exchange chromatography and of the heparin affinity chromatography, respectively, in which the plasma protease had been selectively removed by lysine- Sepharose or in which the vitamin K-dependent factors had been selectively removed by calcium chloride elution showed the highest stability. Even after 30 days the vWF multimer patterns had not changed in these samples, while in the samples which had not been subjected to a lysine-Sepharose chromatography or to a calcium chloride elution, respectively, the occurrence of proteolytic vWF degradation products could be recognized in dependence on the duration of time. For maintaining the stability of the high-molecular vWF multimers, thus in particular the removal of plasma proteins present in the starting material is necessary, since the former greatly affect or lower, respectively, the storage stability.

EXAMPLE 8

Increasing the Stability of the Purified Factor VIII Complex by the Addition of Purified High-molecular vWF Multimers Different amounts of purified p-vWF/HMW or r-vWF/HMW were added to various factor VIII- or factor VIII/vWF-complex-containing fractions obtained by chromatographic purification steps, the mixtures were incubated at 4° C. and room temperature over a period of time of up to 40 days, and the vWF multimer composition as well as the factor VIII:C and vWF-ristocetin cofactor activities were determined after 0, 1, 5, 10, 20, 25, 30, 35 and 40 days. The stability of the vWF multimers as well as the specific ristocetin cofactor activity were the best in those eluates in which plasma proteins, in particular plasma proteases, had been removed by a preceding chromatography. By the addition of a vWF/HMW-containing fraction to the individual factor VIII or factor VIII/vWF-containing fractions or to the starting material from cryoprecipitate, respectively, in particular in those fractions which had a low stability according to Example 7, an improvement of the stability could be attained. Depending on the addition of the amount of high-molecular vWF multimers, the occurrence of proteolytic degradation products as well as a reduction of the specific activity of factor VIII and vWF activity could be temporally retarded.

EXAMPLE 9

Virus Inactivation of Purified Factor VIII/vWF-complex and of Purified Factor VIII/vWF-complex after the Addition of High-molecular vWF Multimers, Respectively, and Determination of Factor VIII:C and vWF-ristoCoF Activities Individual fractions from the chromatographic purification steps as well as fractions to which purified high-molecular vWF multimers or albumin, respectively, had been added, were subjected to a virus inactivation method. For this purpose, the samples were heated for 10 h at 60° C., and subsequently again further incubated for 1 h at 80° C. Subsequently, a vWF multimer analysis and a determination of the activity of factor VIII:C and of the specific vWF platelet agglutination activity were carried out. It has been shown that particularly those samples which had a particularly high portion of high-molecular vWF multimers and not any low-molecular vWF degradation products after heparin affinity chromatography, and which further had a high specific ristocetin cofactor activity, exhibited the least activity losses of factor VIII and vWF. Even in samples to which a certain amount of purified high-molecular vWF multimers had additionally been added, the activity loss after the inactivation method was 10% at the most. In those samples to which albumin had been added, the specific activity decreased upon the addition of the stabilizer and then, once more, after the inactivation method. By this it could be demonstrated that by the presence of vWF/HMW exclusively, or by the addition of high-molecular vWF multimers, respectively, the stability of the proteins in the factor VIII/vWF-complex can be increased substantially without substantially reducing the specific activity.

We claim:

1. A method for treating hemophilia A, comprising administering to a patient a stable Factor VIII/vWF-complex that has a platelet agglutination activity of at least 50 U/mg von Willebrand Factor antigen, wherein (i) the Factor VIII/vWF-complex comprises high-molecular vWF multimers and (ii) the composition is free from low-molecular vWF molecules and from proteolytic degradation products.

2. The method according to claim 1, wherein the complex has a molar riatio of Factor VIII to vWF between 0.01 and 100.

3. The method according to claim 1, wherein the complex has a molar ratio of Factor VIII to vWF between 0.05 and 1.

4. The method according to claim 1, further comprising high-molecular plasmatic vWF multimers having doublet structure.

5. The method according to claim 1, further comprising high-molecular recombinant vWF multimers having singlet structure.

6. The method according to claim 1, wherein the high-molecular vWF molecules have high structural integrity.

7. The method according to claim 1, wherein the Factor VIII/vWF-complex is free from plasma proteins, fibrinogen and fibronectin.

8. The method according to claim 7, wherein the plasma proteins are plasma proteases.

9. The method according to claim 1, wherein the Factor VIII/vWF-complex is storage-stable in solution.

10. The method according to claim 1, wherein the Factor VIII/vWF-complex has been treated to inactivate viruses.

11. The method according to claim 1, wherein the Factor VIII/vWF-complex has been treated to remove viruses.

12. A method for treating von Willebrand syndrome, comprising administering to a patient an effective dose of a stable Factor VIII/vWF-complex that has a platelet agglutination activity of at least 50 U/mg von Willebrand Factor antigen, wherein (i) the Factor VIII/vWF-complex comprises high-molecular vWF multimers and (ii) the composition is free from low-molecular vWF molecules and from proteolytic degradation products.

13. The method according to claim 12, wherein the complex has a molar ratio of Factor VIII to vWF between 0.01 and 100.

14. The method according to claim 12, wherein the complex has a molar ratio of Factor VIII to vWF between 0.05 and 1.

15. The method according to claim 12, further comprising high-molecular plasmatic vWF multimers having doublet structure.

16. The method according to claim 12, further comprising high-molecular recombinant vWF multimers having singlet structure.

17. The method according to claim 12, wherein the high-molecular vWF molecules have high structural integrity.

18. The method according to claim 12, wherein the Factor VIII/vWF-complex is free from plasma proteins, fibrinogen and fibronectin.

19. The method according to claim 18, wherein the plasma proteins are plasma proteases.

20. The method according to claim 12, wherein the Factor VIII/vWF-complex is storage-stable in solution.

21. The method according to claim 12, wherein the Factor VIII/vWF-complex has been treated to inactivate viruses.

22. The method according to claim 12, wherein the Factor VIII/vWF-complex has been treated to remove viruses.

23. A stable, purified Factor VIII/von Willebrand Factor (vWF)-complex that has a platelet agglutination activity of at least 50 U/mg von Willebrand Factor antigen, wherein the complex comprises high-molecular vWF multimers that are free from (i) low-molecular vWF molecules and (ii) proteolytic vWF degradation products.

24. The stable Factor VIII/vWF-complex according to claim 23, wherein the complex has a molar ratio of Factor VIII to vWF between 0.01 and 100.

25. The stable Factor VIII/vWF-complex according to claim 24, wherein the molar ratio of Factor VIII to vWF is between 0.05 and 1.

26. The stable Factor VIII/vWF-complex according to claim 23, further comprising high-molecular plasmatic vWF multimers having doublet structure.

27. The stable Factor VIII/vWF-complex according to claim 23, further comprising high-molecular recombinant vWF multimers having singlet structure.

28. The stable Factor VIII/vWF-complex according to claim 27, wherein the high-molecular vWF molecules have a high structural integrity.

29. The stable Factor VIII/vWF-complex according to claim 23, wherein the Factor VIII/vWF-complex is free from plasma proteins, fibrinogen and fibronectin.

30. The stable Factor VIII/vWF-complex according to claim 29, wherein the plasma proteins are plasma proteases.

31. The stable Factor VIII/vWF-complex according to claim 23, wherein the Factor VIII/vWF-complex is storage-stable in solution.

32. The stable Factor VIII/vWF-complex according to claim 23, wherein the Factor VIII/vWF-complex has been treated to inactivate viruses.

33. The stable Factor VIII/vWF-complex according to claim 23, wherein the Factor VIII/vWF-complex has been treated to remove viruses.

34. A stable, virus-safe Factor VIII/vWF-complex concentrate products that has a platelet agglutination activity of at least 50 U/mg von Willebrand Factor antigen, wherein (i) the complex comprises high-molecular vWF multimers of high structural integrity, and (ii) the vWF multimers have singlet or doublet structure and are free from proteolytical vWF degradation.

35. The stable, virus-safe Factor VIII/vWF-complex concentrate according to claim 34, wherein the complex has a molar ratio of Factor VIII to vWF between 0.01 and 100.

36. The stable, virus-safe Factor VIII/vWF-complex concentrate according to claim 35, wherein the molar ratio of Factor VIII to vWF is between 0.05 and 1.

37. The stable, virus-safe Factor VIII/vWF-complex concentrate according to claim 36, wherein the aid Factor VIII/vWF-complex concentrate is free from plasma proteins and free from microbiological and molecular-biological pathogens.

38. The stable, virus-safe Factor VIII complex concentrate according to claim 37, wherein the plasma proteins are plasma proteases.

39. A pharmaceutical composition comprising a stable Factor VIII/vWF-complex that has a platelet agglutination activity of at least 50 U/mg vWG:Ag, wherein the complex comprises high-molecular vWF multimers, and wherein the composition is free from low-molecular vWF molecules and from proteolytic vWF degradation products.

40. The pharmaceutical composition according to claim 39, further comprising a physiologically acceptable carrier.

\* \* \* \* \*